(12) United States Patent
Samusawa et al.

(10) Patent No.: US 10,024,781 B2
(45) Date of Patent: Jul. 17, 2018

(54) STRESS CORROSION CRACK TEST METHOD IN ALCOHOL ENVIRONMENT

(71) Applicant: JFE STEEL CORPORATION, Tokyo (JP)

(72) Inventors: Italu Samusawa, Kurashiki (JP); Kazuhiko Shiotani, Kurashiki (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 15/121,501

(22) PCT Filed: Feb. 19, 2015

(86) PCT No.: PCT/JP2015/000801
§ 371 (c)(1),
(2) Date: Aug. 25, 2016

(87) PCT Pub. No.: WO2015/129215
PCT Pub. Date: Sep. 3, 2015

(65) Prior Publication Data
US 2016/0363526 A1 Dec. 15, 2016

(30) Foreign Application Priority Data

Feb. 25, 2014 (JP) .................................. 2014-033852
Oct. 24, 2014 (JP) .................................. 2014-216851

(51) Int. Cl.
*G01N 3/32* (2006.01)
*G01N 17/04* (2006.01)
*G01N 3/08* (2006.01)

(52) U.S. Cl.
CPC ............... *G01N 17/04* (2013.01); *G01N 3/08* (2013.01); *G01N 3/32* (2013.01);
(Continued)

(58) Field of Classification Search
CPC .... G01N 17/04; G01N 3/08; G01N 2203/006; G01N 2203/0236; G01N 2203/0242;
(Continued)

(56) References Cited

U.S. PATENT DOCUMENTS 7,387,031 B1 * 6/2008 Perrin ..................... G01N 3/18
73/820
8,513,020 B2 * 8/2013 Hehn ...................... G01N 3/20
422/53

(Continued)

FOREIGN PATENT DOCUMENTS

CN 104792689 A 7/2015
CN 104964911 A 10/2015
(Continued)

OTHER PUBLICATIONS

May 19, 2017 Office Action issued in Korean Patent Application No. 10-2016-7026119.
(Continued)

*Primary Examiner* — Harshad R Patel
*Assistant Examiner* — Brandi Hopkins
(74) *Attorney, Agent, or Firm* — Oliff PLC

(57) ABSTRACT

A stress corrosion crack test method for evaluating the stress corrosion crack susceptibility of a steel material in alcohol. The method includes filling a cell containing a uniaxial tensile test piece of the steel material with an alcohol solution containing carboxylic acid: 0.1 mmol/L or more and less than 40 mmol/L, chloride ions: 0.05 mg/L or more and less than 300 mg/L, and water: 0.1 vol. % or more and less than 5 vol. %. Additionally, the method includes applying a fluctuating stress at a frequency of $2.0 \times 10^{-5}$ Hz or more and $2.0 \times 10^{-2}$ Hz or less to the uniaxial tensile test piece in the tensile direction. The maximum stress being equal to or more than the yield strength and less than the tensile strength (Continued)

at a test solution temperature, and the minimum stress being 0% or more and 90% or less of the yield strength.

16 Claims, 1 Drawing Sheet

(52) U.S. Cl.
CPC ............... *G01N 2203/006* (2013.01); *G01N 2203/0062* (2013.01); *G01N 2203/0069* (2013.01); *G01N 2203/024* (2013.01); *G01N 2203/0236* (2013.01); *G01N 2203/0242* (2013.01)

(58) Field of Classification Search
CPC ..... G01N 2203/0069; G01N 2203/024; G01N 2203/0062; G01N 17/006; G01N 33/20; G21C 17/00; G21C 19/207; C22C 38/00; C22C 38/06; C22C 38/002; C22C 38/12; C22C 38/16; C22C 38/60; C22C 38/02; C22C 38/14; C22C 38/08; C22C 38/04; C21D 8/0226; C21D 8/0263
See application file for complete search history.

(56) References Cited

U.S. PATENT DOCUMENTS

| | | | |
|---|---|---|---|
| 2005/0167014 A1* | 8/2005 | Yamauchi | G01N 17/006 148/606 |
| 2008/0093584 A1 | 4/2008 | Kwon et al. | |
| 2016/0161395 A1* | 6/2016 | Kim | G21C 17/00 73/799 |

FOREIGN PATENT DOCUMENTS

| | | |
|---|---|---|
| JP | 2006-029977 A | 2/2006 |
| JP | 2012-083115 A | 4/2012 |
| JP | 2015-175790 A | 10/2015 |
| KR | 10-1993-0013713 | 7/1993 |
| KR | 10-2008-0035275 | 4/2008 |

OTHER PUBLICATIONS

J. Torkkeli, et al., "Mechanistic Study of Stress Corrosion Cracking of Carbon Steel in Ethanol", Materials and Corrosion, Oct. 2013, vol. 64, Issue 10, pp. 866-875.
F. Gui, "Evaluation of Ammonia Hydroxide for Mitigating Stress Corrosion Cracking of Carbon Steel in Fuel Grade Ethanol", NACE International Corrosion Conference and Expo, Paper No. 11138, (2011).
X. Lou, "Film Breakdown and Anodic Dissolution During Stress Corrosion Cracking of Carbon Steel in Bioethanol", Journal of the Electrochemical Society., 157, pp. C86-C94 (2010).
F. Gui, "Localized Corrosion of Carbon Steel and Its Implications on the Mechanism and Inhibition of Stress Corrosion Cracking in Fuel-Grade Ethanol", Corrosion, vol. 66, No. 12, pp. 125001-1-125001-12.
Mar. 31, 2015 International Search Report issued in International Application No. PCT/JP2015/000801.
Jan. 31, 2017 Office Action issued in Japanese Patent Application No. 2016-505050.
Nov. 23, 2017 Notice of Allowance issued in Korean Patent Application No. 10-2016-7026119.
Apr. 2, 2018 Office Action issued in Chinese Application No. 201580010002.1.

* cited by examiner

US 10,024,781 B2

STRESS CORROSION CRACK TEST METHOD IN ALCOHOL ENVIRONMENT

This is a national stage application of International Application No. PCT/JP2015/000801, which was filed on Feb. 19, 2015, and claims priority to JP 2014-216851, which was filed on Oct. 24, 2014, and JP 2014/033852, which was filed on Feb. 25, 2014. The disclosures of the prior applications are hereby incorporated by reference herein in their entirety.

TECHNICAL FIELD

The present disclosure relates to a test method which is capable of evaluating the stress corrosion crack (hereinafter, referred to as SCC) susceptibility of a steel material by experimentally simulating the stress corrosion crack of a steel material which is used in an alcohol environment.

BACKGROUND ART

Among the various kinds of bioalcohol, for example, bioethanol is manufactured mainly by degrading and refining the sugar of, for example, corn or wheat. Nowadays, bioethanol is widely used in the world as an alternate fuel to petroleum (gasoline) or as a fuel to be mixed with gasoline, and the amount of bioethanol used tends to increase year by year. For example, in a process of storing and transporting bioethanol or in a process of mixing bioethanol with gasoline, a steel material is used. However, since bioethanol is highly corrosive to steel material, that is, since an SCC tends to be generated in a portion of a steel material in which there is a high residual stress or which is exposed to a fluctuating load, it is difficult to handle bioethanol.

The fact that an extremely small amount of carboxylic acid such as acetic acid exists as an impurity in a process of manufacturing bioethanol and the fact that bioethanol absorbs water, dissolved oxygen, and chloride ions in storage contribute to an increase in the corrosiveness of bioethanol. Therefore, there is a demand for an SCC test method for correctly evaluating the SCC susceptibility of a steel material in a bioalcohol environment.

For example, Non Patent Literature 1 and Non Patent Literature 2 give reports regarding a method for evaluating SCC susceptibility on the basis of the state of a fracture surface, after fracturing, which has been generated by applying strain to a tensile test piece at a constant strain rate of $2\times10^{-6}$ in/s to $8\times10^{-7}$ in/s.

In addition, for example, Non Patent Literature 3 gives a report regarding a method for evaluating SCC susceptibility on the basis of a crack growth distance in a test in which a fluctuating load corresponding to 60% to 80% of the tensile strength of a steel material at a frequency of $1.4\times10^{4}$ Hz is applied to a tensile fatigue test piece provided with a precrack in a simulated bioethanol solution.

CITATION LIST

Non Patent Literature

NPL 1: F. Gui, J. A. Beavers, and N. Sridhar: Evaluation of ammonia hydroxide for mitigating stress corrosion cracking of carbon steel in fuel grade ethanol, NACE Corrosion Paper, No. 11138 (2011)

NPL 2: X. Lou, J. D. Yang, and Preet M. Singh: Film breakdown and anodic dissolution during stress corrosion cracking of carbon steel in bioethanol, J. Electrochem. Soc., 157, C86, (2010)

NPL 3: F. Gui, N. Sridhar, and J. A. Beavers: Localized corrosion of carbon steel and its implications on the mechanism and inhibition of stress corrosion cracking in Fuel-grade ethanol, Corrosion, Vol. 66, No. 12, 125001 (2010)

SUMMARY

Technical Problem

However, in the case of the test method disclosed in Non Patent Literature 1 or Non Patent Literature 2, it is not possible to simulate an actual SCC in which a crack grows due to high residual stress and a fluctuating load. That is, in the case of this method, the generation of a newly-formed surface always occurs at a crack tip while strain continues to be applied at a constant strain rate, which is an SCC environment harsher than an actual environment, and thus there is a risk in that it may not be possible to correctly evaluate the actual SCC susceptibility of a steel material.

In addition, since a crack is forcibly generated by applying strain in the test method described above while a crack is generated in an actual environment due to a stress concentration in a portion in which localized corrosion occurs, it is difficult to say that an SCC environment in bioalcohol is simulated. That is, there is a risk in that it may not be possible to correctly evaluate the actual SCC susceptibility of a steel material.

In addition, in the case of the test method for evaluating SCC susceptibility disclosed in Non Patent Literature 3, since the growth of a crack, which has been artificially provided, is evaluated while a fluctuating load cycle is applied, the influence of the SCC on a crack growth process is taken into consideration. However, since no consideration is given to the crack generation process, the method is insufficiently effective for comprehensively evaluating SCC susceptibility.

In addition, since the maximum test load is within an elastic region when considering the test piece at a macro level, and since the test is performed at a lax cycle, the test takes many days because the crack growth rate is low, which makes it difficult to complete the evaluation in a short time. An object is to provide an SCC test method with which it is possible to evaluate a steel material in a bioalcohol environment in a short time by experimentally simulating an SCC environment in bioalcohol.

Solution to Problem

Therefore, the present inventors, in order to solve the problems described above, diligently conducted research and investigations, and, as a result, obtained the following solution to the problems.

[1] A stress corrosion crack test method in an alcohol environment, the method being a test method for evaluating the stress corrosion crack susceptibility of a steel material in alcohol and including filling a cell containing a uniaxial tensile test piece of the steel material with an alcohol solution containing carboxylic acid: 0.1 mmol/L or more and less than 40 mmol/L, chloride ions: 0.05 mg/L or more and less than 300 mg/L, and water: 0.1 vol. % or more and less than 5 vol. % and applying a fluctuating stress at a frequency of $2.0\times10^{-5}$ Hz or more and $2.0\times10^{-2}$ Hz or less to the uniaxial tensile test piece in the tensile direction, in which the maximum stress is equal to or more than the yield strength at a test solution temperature and less than the tensile strength at the test solution temperature, and in which the minimum stress is equal to or more than 0% and equal to or less than 90% of the yield strength at the test solution temperature.

[2] The stress corrosion crack test method in an alcohol environment according to item [1], in which the test solution temperature is 0° C. or higher and lower than 50° C.

[3] The stress corrosion crack test method in an alcohol environment according to item [1] or [2], in which the test solution has a dissolved oxygen concentration of 1 mg/L or more.

[4] The stress corrosion crack test method in an alcohol environment according to any one of items [1] to [3], in which the maximum stress continues to be applied for 30 seconds or more after the fluctuating stress has reached the maximum stress.

[5] The stress corrosion crack test method in an alcohol environment according to any one of items [1] to [4], in which the uniaxial tensile test piece has a notch in a parallel part of the test piece.

Here, "alcohol" which may be used in the test according to the present disclosure refers to an aliphatic monohydric alcohol, and, specifically, for example, methanol, ethanol, propanol, and butanol can preferably be used.

In addition, "carboxylic acid" which may be used in the test according to the present disclosure refers to a saturated fatty acid, and, specifically, for example, formic acid, acetic acid, propionic acid, and butyric acid can preferably be used.

In addition, "chloride ions" which may be used in the test according to the present disclosure refers to Cl$^-$ ions contained in an inorganic salt, and, as specific examples of an inorganic salt, lithium chloride, sodium chloride, and calcium chloride can preferably be used.

Advantageous Effects

According to the disclosed embodiments, it is possible to provide an SCC test method with which it is possible to evaluate a steel material in a bioalcohol environment in a short time by experimentally simulating an SCC environment in bioalcohol.

DESCRIPTION OF EMBODIMENTS

Figure 1:
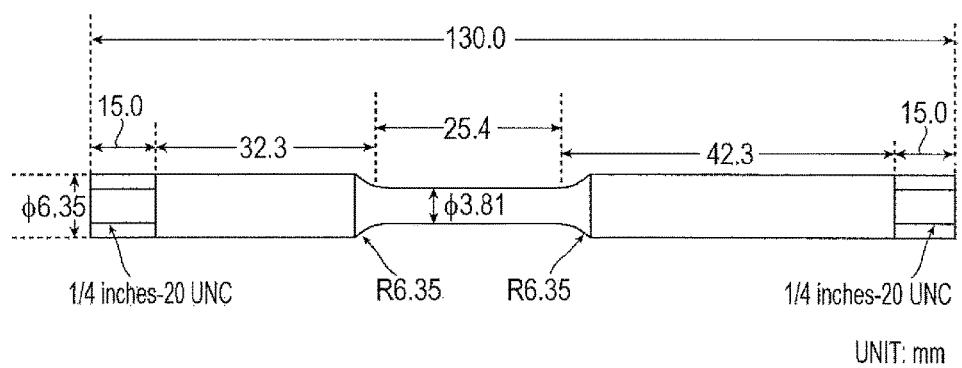
FIG. 1 is a diagram illustrating an example of the shape of a stress corrosion crack test piece.

Exemplary embodiments of the present disclosure will be described specifically hereafter.

The present inventors conducted investigations regarding the generating mechanism of an SCC in a bioalcohol environment, and, as a result, obtained the following knowledge.

Generally, since an oxide film can stably exist on the surface of a steel material in alcohol, and since the surface of the steel material is protected with this oxide film, a corrosion reaction scarcely progresses. However, in the case where, for example, a portion in the vicinity of a weld zone is located at a position at which a fluctuating load occurs in the operation of, for example, a transporting pipe, and in the case where there is a high residual stress in the portion, for example, in the vicinity of the weld zone, the surface oxide film is mechanically ruptured because the portion is locally subjected to a stress in a plastic region. Since selective anodic dissolution occurs in this portion in which an oxide film has been ruptured, a crack is generated.

Moreover, in the case of a structure which is exposed to an environment in which a fluctuating load is applied for a long time, since local corrosion and film regeneration are repeated many times in the portion in which an oxide film has been ruptured, it is not possible to maintain the structure due to the progress of crack growth. A crack growth process will be described in detail hereafter. First, an anodic dissolution reaction occurs in a crack which has been generated of late because the crack has a newly-formed surface. However, since a reaction in which an oxide film is regenerated occurs at the same time, anodic dissolution in the depth direction (crack growth) does not occur in large.

However, since the oxide film is ruptured again because local stress in a plastic region is applied again due to the fluctuating load, anodic dissolution occurs. Since anodic dissolution progresses in such a manner, the crack having the increased depth is exposed to a stress concentration at a higher level. In addition, since it is difficult to supply oxygen to the crack tip, an oxide film is insufficiently generated.

Moreover, since a corrosion reaction is more likely to progress at the crack tip, which is a selective anodic portion, because of the difference in oxygen concentration between the crack tip and the surface of the steel material and the existence of chloride ions and carboxylic acid, crack growth is promoted due to an accelerated dissolution reaction. It is considered that, since it is not possible to maintain the structure, fracturing finally occurs. The present inventors, on the basis of the knowledge regarding the mechanism obtained as described above, established the following conditions in order to make it possible to perform an evaluation test in a short time by experimentally simulating an SCC environment in bioalcohol.

In some exemplary embodiments, the test method includes filling a cell containing a uniaxial tensile test piece of the steel material with an alcohol solution containing carboxylic acid: 0.1 mmol/L or more and less than 40 mmol/L, chloride ions: 0.05 mg/L or more and less than 300 mg/L, and water: 0.1 vol. % or more and less than 5 vol. % and applying a fluctuating stress in the tensile direction of the uniaxial tensile test piece. In the test method according to the disclosed embodiments, the alcohol solution environment simulates a bioalcohol corrosive environment, and the application of stress by using fluctuating stress simulates the stress which is inevitably generated due to the operation of a facility.

Hereafter, the reasons for the limitations on the test environment conditions will be described. Corrosion by bioalcohol depends strongly on the concentrations of the corrosion factors in the alcohol solution.

First, carboxylic acid, which is a factor promoting local corrosion in bioethanol, has the functions of dissolving an oxide film on the surface of a steel material and inhibiting the regeneration of an oxide film. In a load environment in which a surface oxide film is mechanically ruptured, film dissolution by carboxylic acid such as acetic acid is not always necessary for crack generation. However, the function of inhibiting film regeneration by carboxylic acid at the crack tip is necessary for crack growth. However, in the case where the carboxylic acid concentration is less than 0.1 mmol/L, the function of inhibiting oxide film regeneration is insufficient. In addition, in the case where the carboxylic acid concentration is 40 mmol/L or more, film dissolution spreads across a wide area, which results in overall corrosion. Therefore, the carboxylic acid concentration is set to be 0.1 mmol/L or more and less than 40 mmol/L, or preferably 0.1 mmol/L or more and less than 30 mmol/L.

In addition, chloride ions, which are also a factor promoting local corrosion in bioalcohol, have the function of promoting an anodic reaction in a portion of a steel material in which an oxide film is dissolved. However, in the case where the chloride ion concentration is less than 0.05 mg/L, corrosion is not promoted. Therefore, the chloride ion concentration is set to be 0.05 mg/L or more, or preferably 0.1 mg/L or more. On the other hand, in the case where the chloride ion concentration is 300 mg/L or more, since overall corrosion occurs because corrosion is excessively promoted, a stress corrosion crack is not generated. Therefore, the chloride ion concentration is set to be less than 300 mg/L. Here, it is preferable that the chloride ion concentration be 0.1 mg/L or more and less than 270 mg/L.

In addition, water also makes a large contribution to corrosion behavior in bioalcohol. That is, water is involved in an oxide film dissolving process and functions as a transporter for transporting dissociated protons of carboxylic acid. In the case where the water concentration is less than 0.1 vol. %, since the amount is insufficient to transport the dissociated protons in the solution, corrosion is not generated because an oxide film on the surface of the steel material is not dissolved. On the other hand, in the case where the water concentration is 5 vol. % or more, since the dissociated protons of carboxylic acid are uniformly distributed across the surface of the steel material, general corrosion occurs. Therefore, the water concentration is set to be 0.1 vol. % or more and less than 5 vol. %, or preferably 0.3 vol. % or more and less than 3 vol. %.

Moreover, since dissolved oxygen in the test solution contributes to the generation of an oxide film, it is preferable that the dissolved oxygen concentration be 1 mg/L or more, or more preferably 5 mg/L or more. On the other hand, an excessively high dissolved oxygen concentration causes an increase in the size of a test apparatus, which decreases the versatility of the test. In addition, since it is not assumed that the dissolved oxygen concentration may be 1000 mg/L or more in the environment of a practical bioalcohol-related facility, it is preferable that the upper limit of the dissolved oxygen concentration be less than 1000 mg/L. It is more preferable that the dissolved oxygen concentration be 5 mg/L or more and less than 800 mg/L.

In addition, generally, bioalcohol is used in the form of a mixture with gasoline. Although gasoline does not influence corrosion in bioalcohol, less than 30 vol. % of gasoline may be added in order to simulate the mixed state.

Hereafter, stress conditions will be described. It is considered that an SCC in bioalcohol grows by a mechanism in which the occurrence of slip caused by a stress concentration and anodic dissolution are repeated. Moreover, a newly-formed surface, which makes a large contribution to the mechanism, is generated intermittently or at a fluctuating rate under the influence of an anodic dissolution reaction. In addition, an anodic dissolution reaction is subjected to the influence of the generation rate of a newly-formed surface. It is considered that an anodic dissolution reaction markedly progresses in the case where the regeneration rate of an oxide film on a newly-formed surface is lower than the generation rate of a newly-formed surface.

That is, in order to experimentally simulate an SCC environment in which a steel material is used in a bioalcohol environment, it is necessary to set an environment in which a stress concentration area is subjected to a load sufficient to cause local slip and in which the occurrence of slip and an anodic dissolution rate influence each other. Moreover, after stress has been relaxed and a sufficient oxide film has been regenerated at a crack tip and in the vicinity of the crack tip, in the case where the film is selectively ruptured at the crack tip due to an increase in stress, an anodic dissolution reaction at the crack is accelerated.

Therefore, a fluctuating stress was chosen for applying to a steel material in a single tensile direction. By using a fluctuating stress, it is possible to complete the evaluation in a short time by accelerating crack growth while simulating an SCC mechanism. In order to promote crack growth, a fluctuating stress is applied under the conditions that the maximum stress corresponds to a stress equal to or more than 100% of the yield strength of the steel material at a test solution temperature and less than 100% of the tensile strength of the steel material at the test solution temperature, and that the minimum stress corresponds to a stress equal to or more than 0% and equal to or less than 90% of the yield strength of the steel material at the test solution temperature. In the case where the maximum stress is less than 100% of the yield strength, since a stress in a plastic region is not applied when a crack has not been generated, an oxide film on the surface is not mechanically ruptured. That is, since a local corrosion process which starts from the dissolution of a film by carboxylic acid or chloride ions in an alcohol solution is necessary at a stage prior to the generation of a crack, it takes a long time before the evaluation is started.

Here, in order to avoid mechanical fracturing which is not caused by an SCC, it is also necessary that the maximum stress be less than 100% of the tensile strength. In addition, in the case where the minimum stress is equal to or more than 91% of the yield strength, since an oxide film is not sufficiently regenerated at a crack tip and in the vicinity of the crack tip because stress relaxation does not occur sufficiently in the vicinity of a crack, it is not possible to realize the effect of promoting a selective anodic reaction at the crack tip due to an increase in stress.

On the other hand, in the case where the minimum stress is less than 0% of the yield strength (in the case of a compressive stress), since there is an excessive increase in stress fluctuation amplitude, fracturing due to fatigue fracturing, in which corrosion is not involved, may occur. That is, it is not possible to correctly evaluate the stress corrosion crack susceptibility of a steel material in alcohol. Therefore, the minimum stress is set to be equal to or more than 0% and equal to or less than 90% of the yield strength, or preferably equal to or more than 0% and equal to or less than 80% of the yield strength. In addition, as the yield strength which is used in the present test, a lower yield point, 0.2% offset proof stress, or 0.5% onset proof stress can preferably be used.

In addition, the frequency of the fluctuating stress is set to be $2.0 \times 10^{-5}$ Hz or more and $2.0 \times 10^{-2}$ Hz or less. In the case where the frequency is less than $2.0 \times 10^{-5}$ Hz, since a film rupture frequency is small, it is not possible to sufficiently realize the effect of promoting crack growth. On the other hand, in the case where the frequency is more than $2.0 \times 10^{-2}$ Hz, since there is not a sufficient time for film regeneration in a portion at a crack tip in which a film has been ruptured, crack growth is inhibited. Here, in order to allow film rupture and subsequent anodic dissolution to sufficiently occur due to an increase in stress after stress has been relaxed, it is preferable that the maximum stress be continued to be applied for 30 seconds or more after the stress has reached the maximum stress.

In addition, since the mechanical properties and corrosion reaction rate of a steel material vary in accordance with the test solution temperature, the amount of corrosion and the degree of SCC growth vary with the test solution temperature. In order to simulate the temperature to which a practical bioalcohol facility is exposed, it is preferable that the test solution temperature be 0° C. or higher and lower than 50° C.

As described above, in the test method according to the present disclosed embodiments, by applying the fluctuating stress to a steel material under the conditions described above in the corrosive environment in which a bioalcohol environment is simulated, SCC generation is accelerated while simulating an actual SCC environment.

Here, the disclosed embodiments may be applied to steel materials in various states such as bare steel materials and coated steel materials.

In addition, although there is no particular limitation on the shape of a test piece, it is preferable that the test piece be, for example, a round bar-type tensile test piece, which is illustrated in FIG. 1, having a surface roughness of less than 10 μm in terms of Rz (JIS B 0601 (2001)) in the parallel part thereof. In addition, in order to limit a position at which a crack is generated and to perform evaluation in a decreased time, a notch may be formed in the parallel part of the test piece. In the case where the curvature radius of the notch tip is excessively small, since a crack generation process in a bioalcohol environment is not taken account of, it is not possible to sufficiently evaluate comprehensive SCC susceptibility. Therefore, it is preferable that the curvature radius of the notch tip be 20 μm or more. In addition, the stress applied to the test piece which is provided with a notch is decided on the basis of the yield strength and tensile strength obtained by using a test piece having the same shape and applying a cross section of a parallel part corresponding to that at the position of the notched bottom.

By using the test method according to the present disclosure, it is possible to quantitatively evaluate the SCC susceptibility of an object steel material on the basis of a time from when the test is started until fracturing occurs. Moreover, it is also possible to compare the degrees of the effect of increasing SCC resistance of steel materials which are provided with increased SCC resistance. In addition, even if fracturing does not occur in the test period, by taking out the unbroken test piece and observing its cross section, it is also possible to evaluate its SCC susceptibility on the basis of the crack growth distance.

EXAMPLE 1

Examples will be described hereafter. The present disclosure is not limited to these examples.

By preparing molten steel having the chemical composition given in Table 1 with the balance being Fe and incidental impurities, which simulates the chemical composition used for a general linepipe, by using a vacuum melting furnace or a converter and performing continuous casting, a slab was obtained. Subsequently, by heating the slab to a temperature of 1230° C., by then performing hot rolling with a finisher delivery temperature of 820° C., a steel plate having a thickness of 13 mm was obtained.

TABLE 1

| | | | | | | | | | mass % |
|---|---|---|---|---|---|---|---|---|---|
| C | Si | Mn | P | S | Sol. Al | Cu | Ni | Nb | Ti |
| 0.09 | 0.19 | 0.88 | 0.017 | 0.002 | 0.030 | 0.01 | 0.01 | 0.024 | 0.013 |

A round bar-type uniaxial tensile test piece (whose parallel part had a length of 25.4 mm and a diameter of 3.81 mmϕ) having the shape illustrated in FIG. 1 was taken from such a steel plate, the parallel part of the test piece was polished to be equivalent to #2000 finish, and, optionally, the test piece was provided with a notch (having a depth of 250 μm, a curvature radius of 50 μm, and an angle of 60°). Subsequently, the test piece was subjected to ultrasonic degreasing in acetone for five minutes, subjected to air drying, and fitted to a low-strain-rate tensile test machine.

Here, the yield strength and tensile strength of the steel material at a test temperature was determined before an SCC test was performed. The yield strength (lower yield point) and tensile strength of the present steel material were 411 MPa and 511 MPa, respectively, at a temperature of 25° C. Here, the yield strength (lower yield point) and tensile strength of the steel material which was provided with a notch were 515 MPa and 623 MPa, respectively. The test piece was subjected to stress in accordance with the determined yield strength and the corresponding condition. A cell containing the test piece was filled with the test solution having the corresponding chemical composition and the low-strain-rate tensile test machine was allowed to run for 240 hours. While it is not necessarily deniable that an SCC may be generated in the case where the test time is extended, it is preferable that the test be performed for the test time described above from the viewpoint of the practical utility of the test method.

In the case where fracturing was recognized during the test period, the time when fracturing occurred was recorded. In addition, in the case of a steel material with which fracturing did not occur, the test piece was taken out of the machine after the test has been performed, and the external observation was performed on the test piece by using a microscope in order to determine whether or not a crack was generated. In the case of a test piece in which a crack was recognized, the cross section was observed in order to determine the maximum crack length in the cross section and to calculate a crack growth distance. In the case where the crack length was less than 20 μm, since crack growth was insufficient, the test condition of the case was judged as inappropriate as the condition of SCC susceptibility evaluation. On the basis of the information obtained as described above, the judgment criteria regarding the existence of an SCC were as follows.

⊚: fracturing

○: with a crack (crack length: 20 μm or more)

Δ: with a microcrack (crack length: less than 20 μm)

×: without a crack

Figure 2:
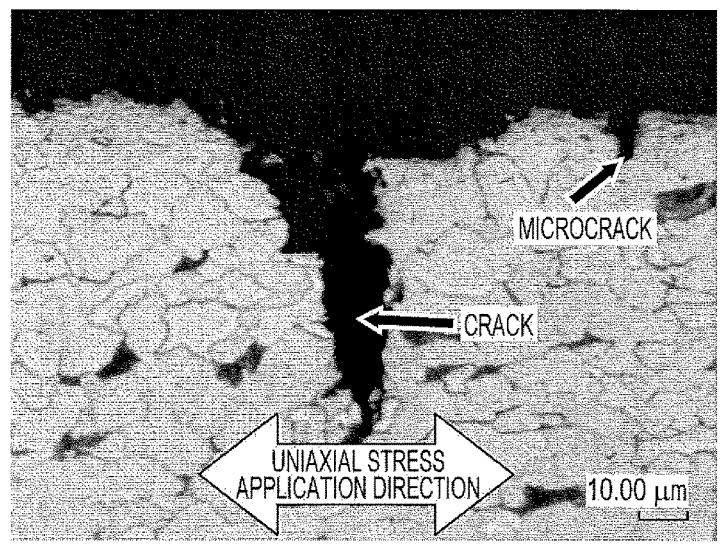
FIG. 2 is a diagram illustrating an image by the microscopic observation of the state in which cracks are generated in the cross section of a test piece after a stress corrosion crack test has been performed.

FIG. 2 is a diagram illustrating an image by the microscopic observation of the state in which cracks are generated in the cross section of a test piece after the test has been performed. After a crack has been generated, as a result of the growth of the crack, a crack having a crack length of 20 μm or more as illustrated at the center of FIG. 2 is observed. On the other hand, in the case where sufficient crack growth does not progress after a crack has been generated, the crack remains a microcrack having a crack length of less than 20 μm as illustrated in the right side of FIG. 2.

The test conditions used are given in Table 2 and Table 3, and the results are given in Table 4.

TABLE 2

| Example | Solution Chemical Composition | | | | | | Temperature (° C.) |
|---|---|---|---|---|---|---|---|
| | Alcohol (vol. %) | Carboxylic Acid (mmol/L) | Chloride Ion (mg/L) | Water (vol. %) | Dissolved Oxygen (ppm) | Other (vol. %) | |
| No. 1 | Ethanol Bal. | Acetic Acid 1.0 | 8 | 1 | 80 | | 25 |
| No. 2 | Ethanol Bal. | Acetic Acid 1.0 | 8 | 1 | 80 | | 25 |
| No. 3 | Ethanol Bal. | Acetic Acid 1.0 | 8 | 1 | 80 | | 25 |
| No. 4 | Ethanol Bal. | Acetic Acid 1.0 | 8 | 1 | 80 | | 25 |
| No. 5 | Ethanol Bal. | Acetic Acid 1.0 | 8 | 1 | 80 | | 25 |
| No. 6 | Ethanol Bal. | Acetic Acid 1.0 | 8 | 1 | 80 | | 25 |
| No. 7 | Ethanol Bal. Methanol 0.5 | Formic Acid 0.2 | 8 | 1 | 80 | | 25 |
| No. 8 | Ethanol Bal. Butanol 2.0 | Acetic Acid 1.0 Butyric Acid 15 | 16 | 1 | 80 | | 25 |
| No. 9 | Ethanol Bal. Methanol 0.5 | Acetic Acid 2.0 | 32 | 1 | 80 | | 25 |
| No. 10 | Ethanol Bal. Methanol 0.5 | Acetic Acid 0.6 | 32 | 1 | 80 | | 25 |
| No. 11 | Ethanol Bal. Methanol 0.5 | Acetic Acid 25 | 32 | 1 | 80 | | 25 |
| No. 12 | Ethanol Bal. Methanol 0.5 | Acetic Acid 2.0 | 1 | 1 | 80 | | 25 |
| No. 13 | Ethanol Bal. Methanol 0.5 | Acetic Acid 2.0 | 240 | 1 | 80 | | 25 |
| No. 14 | Ethanol Bal. Isopropanol 5.0 | Acetic Acid 1.0 Propionic Acid 1.0 | 32 | 1 | 80 | | 25 |
| No. 15 | Ethanol Bal. Methanol 0.5 | Acetic Acid 2.0 | 32 | 0.4 | 80 | | 25 |
| No. 16 | Ethanol Bal. Methanol 0.5 | Acetic Acid 2.0 | 32 | 3 | 80 | | 25 |
| No. 17 | Ethanol Bal. Methanol 0.5 | Acetic Acid 2.0 | 32 | 1 | 15 | | 25 |

| Example | Maximum Loading Stress (%) *Ratio against Lower Yield Point | Minimum Loading Stress (%) *Ratio against Lower Yield Point | Frequency (Hz) | Notch Formation | Duration of Maximum Load of 30 seconds or More | |
|---|---|---|---|---|---|---|
| No. 1 | 110 | 70 | $2.0 \times 10^{-4}$ | | | Example |
| No. 2 | 110 | 70 | $2.0 \times 10^{-3}$ | | | |
| No. 3 | 110 | 70 | $2.0 \times 10^{-2}$ | | | |
| No. 4 | 100 | 70 | $2.0 \times 10^{-3}$ | | | |
| No. 5 | 110 | 20 | $2.0 \times 10^{-3}$ | | | |
| No. 6 | 110 | 70 | $2.0 \times 10^{-3}$ | | ○ (180 seconds) | |
| No. 7 | 110 | 70 | $2.0 \times 10^{-3}$ | | | |
| No. 8 | 110 | 90 | $2.0 \times 10^{-3}$ | | ○ (30 seconds) | |
| No. 9 | 110 | 70 | $2.0 \times 10^{-3}$ | | | |
| No. 10 | 110 | 70 | $2.0 \times 10^{-3}$ | | | |
| No. 11 | 110 | 70 | $2.0 \times 10^{-3}$ | | | |
| No. 12 | 110 | 70 | $2.0 \times 10^{-3}$ | | | |
| No. 13 | 110 | 70 | $2.0 \times 10^{-3}$ | | | |
| No. 14 | 110 | 80 | $2.0 \times 10^{-3}$ | | | |
| No. 15 | 110 | 70 | $2.0 \times 10^{-3}$ | | | |
| No. 16 | 110 | 70 | $2.0 \times 10^{-3}$ | | | |
| No. 17 | 110 | 70 | $2.0 \times 10^{-3}$ | | | |

TABLE 3

| Example | Solution Chemical Composition | | | | | | Temperature (° C.) |
|---|---|---|---|---|---|---|---|
| | Alcohol (vol. %) | Carboxylic Acid (mmol/L) | Chloride Ion (mg/L) | Water (vol. %) | Dissolved Oxygen (ppm) | Other (vol. %) | |
| No. 18 | Ethanol Bal. Methanol 0.5 | Acetic Acid 2.0 | 32 | 1 | 250 | | 25 |
| No. 19 | Ethanol Bal. Methanol 0.5 | Acetic Acid 2.0 | 32 | 1 | 80 | Gasoline 15 | 25 |
| No. 20 | Ethanol Bal. Methanol 0.5 | Acetic Acid 5.0 | 32 | 1 | 80 | | 10 |
| No. 21 | Ethanol Bal. Methanol 0.5 | Acetic Acid 5.0 | 32 | 1 | 80 | | 40 |

TABLE 3-continued

| No. | | | | | | |
|---|---|---|---|---|---|---|
| No. 22 | Ethanol Bal. Methanol 0.5 | Acetic Acid 1.0 | 80 | 1 | 80 | 25 |
| No. 23 | Ethanol Bal. Methanol 0.5 | Acetic Acid 1.0 | 8 | 1 | 80 | 25 |
| No. 24 | Ethanol Bal. Methanol 0.5 | Acetic Acid 1.0 | 8 | 1 | 50 | 25 |
| No. 25 | Ethanol Bal. Methanol 0.5 | Acetic Acid 1.0 | 1 | 1 | 80 | 25 |
| No. 26 | Ethanol Bal. | Acetic Acid 1.0 | 8 | 1 | 80 | 25 |
| No. 27 | Ethanol Bal. | Acetic Acid 1.0 | 8 | 1 | 80 | 25 |
| No. 28 | Ethanol Bal. | Acetic Acid 1.0 | 8 | 1 | 80 | 25 |
| No. 29 | Ethanol Bal. | Acetic Acid 1.0 | 8 | 1 | 80 | 25 |
| No. 30 | Ethanol Bal. Methanol 0.5 | Acetic Acid 0.2 | 0.02 | 0.05 | 15 | 25 |
| No. 31 | Ethanol Bal. Methanol 0.5 | Formic Acid 50 | 240 | 6 | 15 | −5 |
| No. 32 | Ethanol Bal. Methanol 0.5 | Acetic Acid 0.05 | 240 | 6 | 1 | 25 |
| No. 33 | Ethanol Bal. Methanol 0.5 | Acetic Acid 50 | 0.02 | 6 | 0.5 | 60 |
| No. 34 | Ethanol Bal. Methanol 0.5 | Acetic Acid 0.2 | 0.02 | 0.05 | 40 | 25 |

| Example | Maximum Loading Stress (%) *Ratio against Lower Yield Point | Minimum Loading Stress (%) *Ratio against Lower Yield Point | Frequency (Hz) | Notch Formation | Duration of Maximum Load of 30 seconds or More | |
|---|---|---|---|---|---|---|
| No. 18 | 110 | 70 | $2.0 \times 10^{-3}$ | | | Example |
| No. 19 | 110 | 70 | $2.0 \times 10^{-3}$ | | | |
| No. 20 | 110 | 70 | $2.0 \times 10^{-3}$ | | | |
| No. 21 | 110 | 70 | $2.0 \times 10^{-3}$ | | | |
| No. 22 | 110 | 50 | $2.0 \times 10^{-3}$ | | | |
| No. 23 | 110 | 20 | $2.0 \times 10^{-5}$ | | | |
| No. 24 | 110 | 70 | $2.0 \times 10^{-4}$ | Done | | |
| No. 25 | 110 | 20 | $2.0 \times 10^{-3}$ | Done | | |
| No. 26 | 90 | 80 | $2.0 \times 10^{-4}$ | | | Comparative Example |
| No. 27 | 110 | 95 | $2.0 \times 10^{-4}$ | | | |
| No. 28 | 110 | 80 | $1.0 \times 10^{-5}$ | | | |
| No. 29 | 110 | 80 | $8.0 \times 10^{-2}$ | | | |
| No. 30 | 100 | 70 | $2.0 \times 10^{-3}$ | | | |
| No. 31 | 110 | 70 | $2.0 \times 10^{-3}$ | | | |
| No. 32 | 95 | 70 | $2.0 \times 10^{-3}$ | | | |
| No. 33 | 85 | 50 | $2.0 \times 10^{-3}$ | | | |
| No. 34 | 110 | 80 | $2.0 \times 10^{-3}$ | Done | | |

TABLE 4

| Example | Existence of SCC | Fracturing Time (h) | Crack Growth Distance (μm) | |
|---|---|---|---|---|
| No. 1 | ○ | — | 40 | Example |
| No. 2 | ○ | — | 85 | |
| No. 3 | ○ | — | 37 | |
| No. 4 | ○ | — | 44 | |
| No. 5 | ⊙ | 212 | — | |
| No. 6 | ⊙ | 224 | — | |
| No. 7 | ○ | — | 63 | |
| No. 8 | ○ | — | 88 | |
| No. 9 | ⊙ | 197 | — | |
| No. 10 | ○ | — | 81 | |
| No. 11 | ⊙ | 207 | — | |
| No. 12 | ○ | — | 67 | |
| No. 13 | ⊙ | 144 | — | |
| No. 14 | ○ | — | 84 | |
| No. 15 | ○ | — | 103 | |
| No. 16 | ○ | — | 69 | |
| No. 17 | ○ | — | 85 | |
| No. 18 | ⊙ | 156 | — | |
| No. 19 | ⊙ | 193 | — | |
| No. 20 | ⊙ | 219 | — | |
| No. 21 | ⊙ | 239 | — | |
| No. 22 | ⊙ | 190 | — | |
| No. 23 | ○ | — | 45 | |
| No. 24 | ⊙ | 235 | — | |
| No. 25 | ⊙ | 123 | — | |
| No. 26 | Δ | — | 5 | Comparative Example |
| No. 27 | Δ | — | 18 | |
| No. 28 | Δ | — | 14 | |
| No. 29 | Δ | — | 17 | |
| No. 30 | X | — | — | |
| No. 31 | X | — | — | |
| No. 32 | X | — | — | |
| No. 33 | X | — | — | |
| No. 34 | Δ | — | 15 | |

As Table 4 indicates, it is clarified that an SCC was generated in the test piece of any of the examples (Nos. 1 through 25) because the test piece is denoted by (○) in which fracturing did not occur but in which a crack having a length of 20 μm or more was recognized in the cross-sectional view of the parallel part in an image by the microscopic observation as illustrated in FIG. 2 or denoted by (⊙) in which fracturing occurred.

On the other hand, each of the cases (Nos. 26 through 34) of the comparative examples was a case (Δ) of a microcrack having a length of less than 20 μm or a case (x) of no crack, which means that the condition of such a case is inappropriate as the condition of SCC susceptibility evaluation.

The invention claimed is:

1. A stress corrosion crack test method in an alcohol environment, the method being a test method for evaluating the stress corrosion crack susceptibility of a steel material in alcohol, the method comprising:
    filling a cell containing a uniaxial tensile test piece of the steel material with an alcohol solution,
        the alcohol solution containing:
            carboxylic acid: 0.1 mmol/L or more and less than 40 mmol/L, chloride ions: 0.05 mg/L or more and less than 300 mg/L, and water: 0.1 vol. % or more and less than 5 vol. %; and
    applying a fluctuating stress at a frequency of $2.0 \times 10^{-5}$ Hz or more and $2.0 \times 10^{-2}$ Hz or less to the uniaxial tensile test piece in a tensile direction,
    wherein:
        a maximum stress of the fluctuating stress is equal to or more than a yield strength of the steel material at a test solution temperature and less than a tensile strength of the steel material at the test solution temperature, and
        a minimum stress of the fluctuating stress is 0% or more and 90% or less of the yield strength of the steel material at the test solution temperature.

2. The stress corrosion crack test method in an alcohol environment according to claim 1, wherein the test solution temperature is 0° C. or higher and lower than 50° C.

3. The stress corrosion crack test method in an alcohol environment according to claim 2, wherein the alcohol solution has a dissolved oxygen concentration of 1 mg/L or more.

4. The stress corrosion crack test method in an alcohol environment according to claim 3, wherein the maximum stress is continuously applied for 30 seconds or more after the fluctuating stress has reached the maximum stress.

5. The stress corrosion crack test method in an alcohol environment according to claim 4, wherein the uniaxial tensile test piece has a notch in a parallel part of the test piece.

6. The stress corrosion crack test method in an alcohol environment according to claim 3, wherein the uniaxial tensile test piece has a notch in a parallel part of the test piece.

7. The stress corrosion crack test method in an alcohol environment according to claim 2, wherein the maximum stress is continuously applied for 30 seconds or more after the fluctuating stress has reached the maximum stress.

8. The stress corrosion crack test method in an alcohol environment according to claim 7, wherein the uniaxial tensile test piece has a notch in a parallel part of the test piece.

9. The stress corrosion crack test method in an alcohol environment according to claim 2, wherein the uniaxial tensile test piece has a notch in a parallel part of the test piece.

10. The stress corrosion crack test method in an alcohol environment according to claim 1, wherein the alcohol solution has a dissolved oxygen concentration of 1 mg/L or more.

11. The stress corrosion crack test method in an alcohol environment according to claim 10, wherein the maximum stress is continuously applied for 30 seconds or more after the fluctuating stress has reached the maximum stress.

12. The stress corrosion crack test method in an alcohol environment according to claim 11, wherein the uniaxial tensile test piece has a notch in a parallel part of the test piece.

13. The stress corrosion crack test method in an alcohol environment according to claim 10, wherein the uniaxial tensile test piece has a notch in a parallel part of the test piece.

14. The stress corrosion crack test method in an alcohol environment according to claim 1, wherein the maximum stress is continuously applied for 30 seconds or more after the fluctuating stress has reached the maximum stress.

15. The stress corrosion crack test method in an alcohol environment according to claim 14, wherein the uniaxial tensile test piece has a notch in a parallel part of the test piece.

16. The stress corrosion crack test method in an alcohol environment according to claim 1, wherein the uniaxial tensile test piece has a notch in a parallel part of the test piece.

* * * * *